(12) United States Patent
Kantor et al.

(10) Patent No.: US 12,014,806 B2
(45) Date of Patent: Jun. 18, 2024

(54) SYSTEM FOR IMMEDIATE PERSONALIZED TREATMENT OF A PATIENT IN A MEDICAL EMERGENCY

(71) Applicant: INOVYTEC MEDICAL SOLUTIONS LTD, Hod Hasharon (IL)

(72) Inventors: Ehud Kantor, Hod Hasharon (IL); Guye Biron Halpern, Raanana (IL)

(73) Assignee: Inovytec Medical Solutions Ltd., Hod Hasharon (IL)

( * ) Notice: Subject to any disclaimer, the term of this patent is extended or adjusted under 35 U.S.C. 154(b) by 110 days.

(21) Appl. No.: 17/282,573

(22) PCT Filed: Oct. 2, 2019

(86) PCT No.: PCT/IL2019/051077
§ 371 (c)(1),
(2) Date: Apr. 2, 2021

(87) PCT Pub. No.: WO2020/075159
PCT Pub. Date: Apr. 16, 2020

(65) Prior Publication Data
US 2021/0350889 A1   Nov. 11, 2021

(51) Int. Cl.
*G16H 10/65*   (2018.01)
*A61B 5/00*   (2006.01)
(Continued)

(52) U.S. Cl.
CPC ........... *G16H 10/65* (2018.01); *A61B 5/1172* (2013.01); *A61B 5/747* (2013.01); *A61J 7/0084* (2013.01);
(Continued)

(58) Field of Classification Search
CPC ...... G16H 10/65; G16H 20/10; A61B 5/1172; A61B 5/747; A61B 2505/01
See application file for complete search history.

(56) References Cited

U.S. PATENT DOCUMENTS

| 6,564,121 B1 | 5/2003 | Wallace et al. |
| 10,507,167 B1 * | 12/2019 | Bunker ................. G16H 20/13 |

(Continued)

FOREIGN PATENT DOCUMENTS

| CA | 3014319 | 8/2017 |
| EP | 2544584 | 1/2013 |

(Continued)

OTHER PUBLICATIONS

European Search Report dated Aug. 11, 2022.

*Primary Examiner* — Robert A Sorey
*Assistant Examiner* — Kristine K Rapillo
(74) *Attorney, Agent, or Firm* — Renner, Kenner, Greive, Bobak, Taylor & Weber

(57) ABSTRACT

Disclosed is a system designed for providing immediate treatment in medical emergency situations effecting respiratory, cardiac, and/or central nervous system functions. For non-limiting examples, the system may also be used for conditions such as trauma and chronic conditions. The main goal of the system is to provide a person who experiences a medical emergency with personalized treatment that is as close as possible to the treatment that he/she would receive in an emergency room beginning from the moment the event occurs.

15 Claims, 2 Drawing Sheets

(51) Int. Cl.
  *A61B 5/1172*  (2016.01)
  *A61J 7/00*  (2006.01)
  *G16H 20/10*  (2018.01)

(52) U.S. Cl.
  CPC .......... *G16H 20/10* (2018.01); *A61B 2505/01* (2013.01)

(56) References Cited

U.S. PATENT DOCUMENTS

| | | |
|---|---|---|
| 2003/0227386 A1 | 12/2003 | Pulkkinen et al. |
| 2005/0277872 A1* | 12/2005 | Colby, Jr. .............. A61B 5/411 604/67 |
| 2010/0087883 A1 | 4/2010 | Sullivan et al. |
| 2012/0265549 A1 | 10/2012 | Virolainen |
| 2013/0317753 A1 | 11/2013 | Kamen et al. |
| 2016/0093197 A1* | 3/2016 | See ........................ G08B 25/10 340/539.12 |
| 2016/0106362 A1 | 4/2016 | Packer et al. |
| 2017/0293730 A1 | 10/2017 | Fish et al. |

FOREIGN PATENT DOCUMENTS

| | | |
|---|---|---|
| JP | 2005-528967 A | 9/2005 |
| JP | 2011-172948 A | 9/2011 |
| JP | 2012-221508 A | 11/2012 |
| JP | 2013-238971 A | 11/2013 |
| KR | 20160085876 | 7/2016 |
| KR | 20170265020 | 3/2017 |
| WO | 2015068164 | 5/2015 |

\* cited by examiner

SYSTEM FOR IMMEDIATE PERSONALIZED TREATMENT OF A PATIENT IN A MEDICAL EMERGENCY

FIELD OF THE INVENTION

The invention is from the field of equipment for providing emergency medical treatment. In particular the inventions relates to controlling lifesaving equipment to provide the most effective treatment to the patient.

BACKGROUND OF THE INVENTION

Medical emergency situations may occur in various circumstances and affect different body functions such as: trauma injuries, central nerve system injuries (e.g. stroke with apnea), cardiac conditions (e.g. coronary disease or cardiac arrhythmias), respiratory conditions (e.g. pulmonary embolism and chronic obstructive lung disorder, or pulmonary spastic disease), there are also systemic conditions such as anaphylactic shock, that affect multiple body functions.

Immediate medical assistance is critical to the effectiveness of life saving treatment in emergency cases. More often than not, professional medical personnel are not present at the scene of occurrence of an emergency situation, leaving the conduct of first emergency care to a lay person bystander, who is any person physically present at the scene at the time of emergency occurrence that is capable and willing to assist, despite the lack of professional medical qualifications. The layperson care giver is therefore dependent upon lifesaving equipment which must be ultra-user friendly, as it assumes little or no medical knowledge whatsoever of the layperson care giver.

There are three types of critical care devices that are commonly available to provide medical assistance in emergency situation: first aid kits—including bandages and the like; Automated External Defibrillators (AED), which are portable electronic devices that apply electrical shock therapy for the treatment of cardiac arrhythmias; and oxygen therapy devices, which generally are not available to non-professional users, for either supplying oxygen enrichment or active ventilation to a patient, depending on the patient's condition. Devices of these types are familiar to professionals and the general public alike and are available in many different designs and accessible for use in many public venues around the world.

The applicant of this patent application has described in a co-pending PCT application WO 2015/068164 a system that comprises components for applying both electrical shock therapy and oxygen therapy in order to provide decision-assisted critical care to a patient in medical emergency situations in an out of hospital setting.

Prior art devices of this type save many lives however in some cases, if the diagnosis is incorrect or the therapy not correctly applied, they can cause more damage than good. To a certain extent uncertainty as to the correct diagnosis and/or therapy to apply is built into the devices themselves since they are all based on the assumption that the "normal" values of the parameters that their sensors measure and the treatment that should be applied if an abnormal reading is detected are standard treatments that have previously been determined to be effective for the "average" person.

In other words both the diagnosis and the treatment are not based on baseline values of critical parameters for the patient that may differ significantly from those of the population as a whole. This deviation of baseline from average has very special significance in the case of persons having a non-conventional medical history and in which the emergency situation is a result of a known medical condition.

Some examples are:

Some people have abnormal Electrocardiography (ECG) profiles such as an ST elevation. For normal patients ST elevation is indicative of a coronary heart disease and thus a generalized monitoring system will indicate a need for hospitalization when an ST elevation is detected. However, if the medical history of the patient shows this abnormality a different treatment output should be generated.

Patients with chronic lung disease (such as COPD) typically have non-standard oxygen blood saturation rates. A correct clinical decision may be obtained if the baseline saturation data of a patient is used for generating the treatment output A patient with an active Asthma attack will have abnormal respiration rates and $CO_2$ levels. If not compared to the patient's medical history prior art devices may indicate a need to evacuate the patient to a hospital, professional health care center, or health care provider. Integration of the patient's medical history would allow the system to generate other, more accurate treatment outputs, such as the correct dosage of steroids or anti-histamines, or oxygen therapy.

Currently AEDs apply defibrillation to all patients using a set intensity. Consideration of the patient's personal criteria such as age and medical condition would allow adjusting the intensity of the defibrillator for optimizing the results and minimizing collateral damage.

It is a purpose of the present invention to provide a system for providing immediate medical assistance in emergency situations that comprises a personalization function which allows adjusting the treatment mode and medical decisions according to both real time data measurements as well as historical medical background of a specific person.

It is another purpose of the invention to provide a person with personalized treatment from the beginning of a medical emergency that is as close as possible to the treatment provided in an emergency room.

Further purposes and advantages of this invention will appear as the description proceeds.

SUMMARY OF THE INVENTION

In a first aspect the invention is an equipment module for providing immediate personalized treatment to a patient that experiences a medical emergency. The equipment module comprises:
  i) a control unit comprising a processor, data storage elements, dedicated software, input devices, display devices, and communication components;
  ii) a sensor unit comprising sensors that are attachable to the patient's body to collect real-time data relating to the patient's vital signs; and
  iii) an equipment unit comprising components for identifying a patient and for applying treatment.

The equipment module is characterized in that:
  a) the data storage elements contain medical histories previously stored in the control unit for patient's whose identity is known to the system;
  b) the input devices and communication components are configured to obtain medical histories for patient's whose identity is unknown to the system; and
  c) the processor and dedicated software are configured to produce a treatment output based on the comparison of the real-time data to the medical history of the patient by executing the following:
  i) generating instructions for applying sensors from the sensor unit to a patient;
  ii) comparing values of the sensor data with values for corresponding parameters from data in the patient's medical history as well as other information from the patient's medical history to determine the action that should be taken; and
  iii) providing a user with specific instructions for administrating treatment to the patient using equipment from the treatment unit and/or to apply drugs from the personalized drug unit.

In embodiment of the equipment module the processor and dedicated software are further configured to use information received from sensors attached to the body of the patient to evaluate the effectiveness of the treatment.

Embodiments of the equipment module further comprise a personalized drug unit containing drugs that might be needed for immediate administration to patients. The personal drug compartment is electronically locked and can only be unlocked by a signal sent from the processor or by a remotely located physician.

In embodiments of the equipment module the personalized drug unit contains at least one of: glucose tablets, atropine, and nitroglycerin.

In embodiments of the equipment module the action that should be taken is either to apply treatment at the location of the patient or to immediately evacuate the patient to a hospital, professional health care center, or health care provider.

In embodiments of the equipment module evaluation of the effectiveness of the treatment determines whether the treatment should be changed, continued, or discontinued and whether, at the stage the evaluation is being carried out, the patient should be transported to a hospital.

In embodiments of the equipment module the input devices comprise at least one of a keyboard or graphical user interface, configured for imputing information into the processor and data storage elements.

In embodiments of the equipment module the display devices comprise at least one of a computer screen or a graphical user interface configured to display at least one of:
  a) personal information pertinent to the patient;
  b) the medical history of the patient;
  c) data from sensors attached to the patient;
  d) instructions generated by the software in the processor for applying sensors from the sensor unit to the patient; and
  e) instructions generated by the software in the processor for administrating treatment and using equipment from the treatment unit.

In embodiments of the equipment module the communication components are configured for WIFI, cellular, or Bluetooth two way communication between the control unit and the sensors in the sensor unit, the equipment in the treatment unit, and remotely located medical personnel, sensors, and databases and the communication components are configured for one way wired or wireless communication between the control unit and the personalized drug unit.

In embodiments of the equipment module the sensor unit comprises at least one of the following types of sensors: an Electrocardiography (ECG) sensor, a pulse oximeter, an Electroencephalography (EEG) sensor, an ultrasound sensor, a capnograph, a sphygmomanometer, another type of non-invasive blood pressure sensor, a sensor to measure respiration rate, a sensor to measure body temperature, a body weight assessing element, a glucometer, a Hemoglobinometer, an optical sensor configured to observe white blood cells, and a camera or other type of imaging sensor configured to detect asymmetry typical of stroke incidents.

In embodiments of the equipment module the components in the equipment unit for identifying a patient comprise at least one of a fingerprint or retinal scanner, a bar code scanner, a camera for facial recognition, and a document scanner, each of which is connected to the communication components in the control unit.

In embodiments of the equipment module the medical histories for patient's whose identity is unknown to the system are obtained by at least one of the following methods:
  a) by contacting the database of the patient's health care provider;
  b) from a driver's license, identity card, or passport that is carried by the patient;
  c) from a medical alert bracelet worn by the patient;
  d) from testimony of persons accompanying the patient; and
  e) from a specialized pre-installed application containing the person's medical history on his/her personal smartphone.

In a second aspect the invention is a system for providing immediate personalized treatment to a patient that experiences a medical emergency, the system comprising:
  a) an equipment module of claim 1; and
  b) a monitoring module comprising sensors configured to measure a patient's vital signs that are attached to the patient as he/she goes about their daily business, and components configured to wirelessly transmit data collected by the sensors to the control unit in the equipment module.

In embodiments of the system the monitoring module comprises components configured to issue alarm signals and to wirelessly transmit the alarm signals to the equipment module if a medical emergency is detected.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Figure 1:
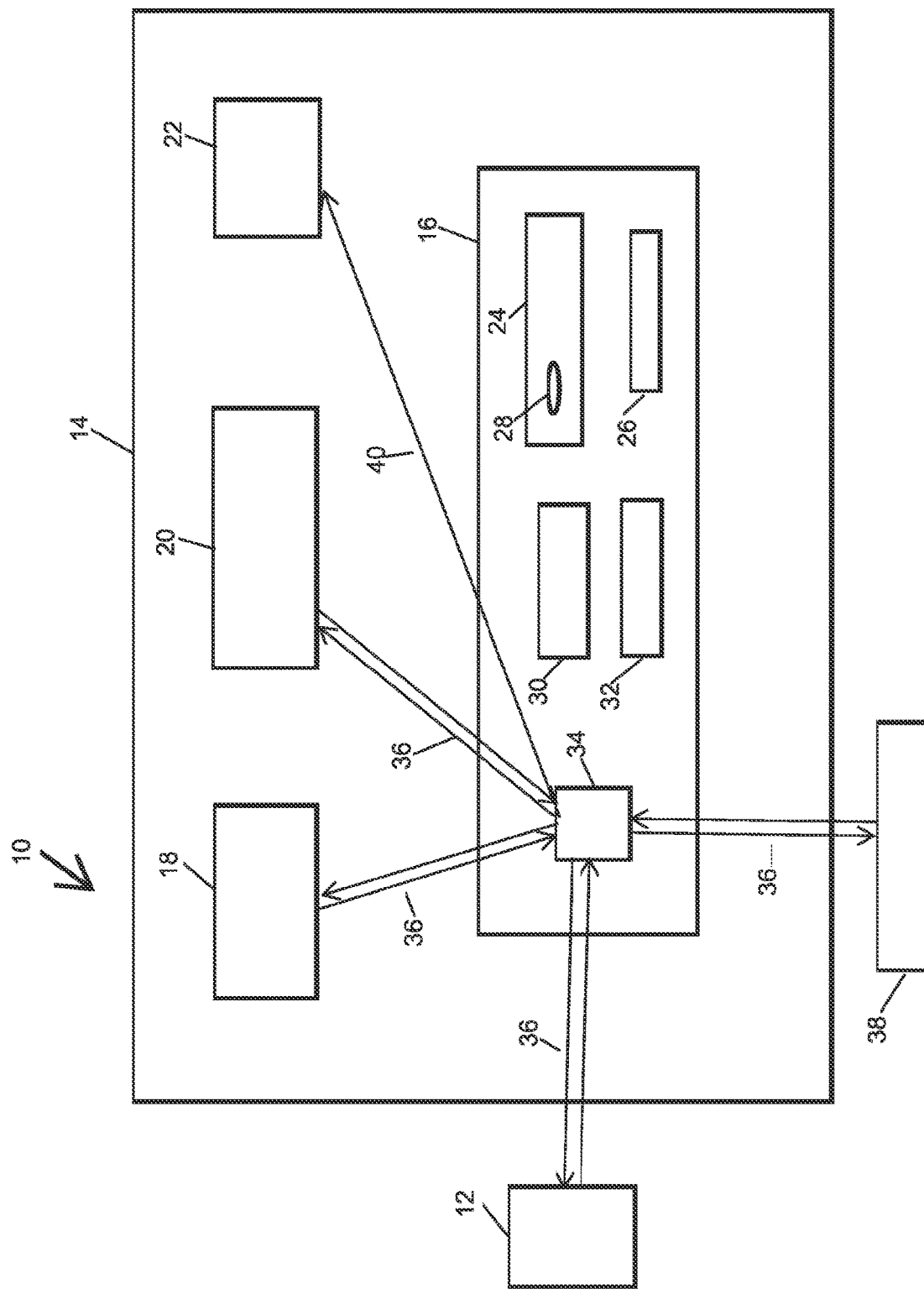
FIG. 1 schematically shows the main components of the system of the invention.

The invention is a system designed for providing immediate treatment in medical emergency situations effecting respiratory, cardiac, and/or central nervous system functions. For a non-limiting example, the system may also be used for conditions such as trauma and chronic conditions. The main goal of the system is to provide a person who experiences a medical emergency personalized treatment that is as close as possible to the treatment that he/she would receive in an emergency room beginning from the moment the event occurs. This is as opposed to present day emergency care systems that provide general treatment that in certain situations may be unnecessary or may even cause damage.

Automation of the treatment procedure allows the system to be used in public and/or private places and medical facilities, for example, home-care, clinics, nursing homes, office buildings, hotels, arenas, and concert halls. Automation of the treatment procedure allows the system to be operated by a person with minimum training; although obviously it can also be employed by professional medical care providers in any venue. If the system is used in a health care facility, such as a doctor's office, retirement home, nursing home, rehabilitation center, or hospital, then the system can be used to routinely collect base line data from visitors, employees, and patients.

The system comprises components that enable the identification of a person needing emergency medical treatment, henceforth known as "the patient". The identification can be performed manually such as by allocating a specific key or by entering a unique number or a letter code for each patient whose identity is known and for which baseline data exists in a database in the system. Alternatively, the identification of a patient may be achieved by an application on a portable device such as a smartphone that is configured to communicate with the system. The identification of a patient may also be carried out automatically by identification means provided in the system that allows the identification of the treated subject once the subject is physically connected to the system, e.g. by fingerprint or retinal scan or facial recognition, or by a signal broadcasted from a dedicated wearable device, e.g. bracelet, that is worn on the patient and is detected when the patient is in close proximity to the system. A patient that is unknown to the system may be identified by information that they carry on them such as a driver's license, identity card, or passport.

In order to gain maximum utility from the system a readily accessible database of the patients health history should be available. For this reason the system is most effectively located in homes, places of business, and similar locations where the identity of many of the persons who are present are known and information relative to the treatment of their known past non-conventional medical histories can be entered into directly into the system. Another scenario that is contemplated is that in certain situations such as boarding an airplane or a cruise ship or checking into a hotel passengers/customers may be required to provide their medical histories that will be stored either locally or at a centralized location that can be accessed by the system.

To use the personalization function the algorithm that is designed to determine the proper treatment comprises a specific step of informing the system whether the patient's history is known (in which case the baseline data for that patient is used) or unknown. If the baseline data for a specific patient is not in the database of the system there are three options: 1. the system can try to gather the necessary data to create a baseline, for example, if access is allowed, by contacting the database of the patient's health care provider; 2. partial information such as previous medical history from a medical alert bracelet, by utilizing a specialized pre-installed application containing the person's medical history on his/her personal smartphone, also testimony of persons accompanying the patient, and information such as gender, approximate weight, height and age can be manually entered; 3. in the absence of personal data the system can rely on the normal values of the measured parameters in the same way that present systems operate.

FIG. 1 schematically shows the main components of the system of the invention. System 10 comprises two modules: a monitoring module 12 and an equipment module 14.

The monitoring module 12 is actually not always an integral part of the system. It represents different types of sensors, e.g. automatic insulin pumps and bracelets that monitor blood pressure and pulse rate, that are attached to a person as he or she goes about their daily business and are equipped to transmit data about the persons vital signs to control unit 16, where they are used to update the baseline data in the persons medical history that is stored in the data storage elements 26. Monitoring module 12 is also configured to issue alarm signals and to transmit them wirelessly to the equipment module 14 if a medical emergency is detected.

Equipment module 14 will be described herein as comprising several units. It is to be understood, however, that the units may not necessarily be physical compartments in equipment module 14 but in some embodiments the division into units may be conceptual to link together different components having similar functions. Similarly, the assignment of the components of the equipment module to a specific unit is for ease of description only and many different arrangements are possible.

In the embodiment shown in FIG. 1, equipment module 14 comprises the following units:
a control unit 16;
a sensor unit 18;
an equipment unit 20; and
a personalized drug unit 22.
Control unit 16 comprises:
a processor 24;
data storage elements 26;
dedicated software 28;
input devices 30, e.g. a keyboard or graphical user interface, configured for imputing information into the processor 24 and data storage elements 26;
display devices 32, e.g. a computer screen or graphical user interface configured to display, inter alia, personal information pertinent to the patient, his/her medical history, data from sensors in the monitoring unit 12, and instructions generated by the software 28 in the processor 24 for applying sensors from sensor unit 18 and for administrating treatment using equipment from treatment unit 20; and
communication components 34 configured for WIFI, cellular, or Bluetooth two way communication 36 between the control unit 16 and the monitoring unit 12, sensors in the sensor unit 18, equipment in the treatment unit 20, and remotely located physicians, other medical personnel, and databases 38 and for one way wired or wireless communication 40 between the control unit 16 and personalized drug unit 22. The internal communication links between the components in control unit 16 are not shown but should be known to persons familiar with the art.

The components of control unit 16 are configured to interact with each other in order to perform the following functions:
to collect and store patient specific data;
to create a file history for each specific patient;
to collect data relating to the vital signs of the patient in real-time from sensors that are included in the monitoring module and are attached to the patient's body; and to produce a treatment output based on the comparison of the real-time data to the medical history file of the patient.

In embodiments of the system all of the functions of the control unit 16 can be provided by dedicated components that are physically incorporated within a housing that contains other units of the system. In other embodiments functions of the control unit 16 can be provided by personal, laptop, or tablet computers, or mobile communication devices such as cellular phones.

Not all embodiments of system 10 comprise all of the components described herein above and some can comprise additional features such as components that allow generation of audible alarms or instructions to a user of the system.

The basic embodiment of sensor unit 18 includes at least one ECG sensor configured to detect ECG signals from the patient and a pulse oximeter to measure blood oxygen saturation.

In addition to these basic sensors the sensor unit 18 may also include one or more of the following: Electroencephalography (EEG) sensors, an ultrasound sensor, a capnograph to measure $CO_2$, a sphygmomanometer to measure blood pressure (or other non-invasive blood pressure sensors), a sensor to measure respiration rate, one or more sensors to measure body temperature, a body weight assessing element (e.g., based on optical sensor input and head scale), a glucometer, a Hemoglobinometer, an optical sensor configured to observe white blood cells, and a sensor (e.g., camera) to detect asymmetry typical of stroke incidents.

Specific embodiments of the sensor unit 18 can be supplied for use with patients suffering from specific known medical conditions. For example the monitoring module for an elderly patient who has previously suffer from a stroke would include EEG sensors and a monitoring module for a child who has had a previous asthma attack would include a capnograph and a sensor to measure respiration rate.

Some patients might not wear a monitoring module 12 but the might connect periodically, e.g. once a day, to a sensor in sensor unit 18 for monitoring purposes such as EEG, blood pressure, and/or heart rate. Further the patient can connect or be connected to sensors in sensor unit 18 for defining a baseline.

The basic embodiment of the equipment unit 20 comprises: components for identifying a patient. The components for identifying a patient comprise, for example, a fingerprint or retinal scanner, a bar code scanner, a camera for facial recognition, and a document scanner, each of which is connected to the communication components 38 in control unit 16.

Embodiments of equipment unit 20 may additionally comprise an automated external defibrillator (AED), a ventilator unit and/or a cooling device, e.g. a fan or thermoelectric cooler. The ventilator unit comprises a pressure/flow sensor, a turbine or other pressure generator, and a delivery means to the patient such as a closed or open mask with or without a reservoir, or an endotracheal tube. The AED comprises an electric circuit connected to an internal battery or an external electricity source for generating current and two ECG chest pads configured to apply electric shock to the patient when required for defibrillation in case shockable cardiac arrhythmia is detected by the ECG sensor/s of the monitoring module. The ventilator unit may also comprise a cylinder of pressurized oxygen or air to provide to the patient pure oxygen, or oxygen enrichment either passive or active, depending on the patient's condition.

The personal drug compartment 22 contains drugs that might be needed for immediate administration to persons having known medical conditions. For example a system in the home or workplace of a diabetic might contain glucose tablets to be administered when the glucose level in his/her blood is extremely low, atropine might be include in the personal drug compartment 22 for use on persons known to have allergic reactions to bee stings or certain foods, and nitroglycerin for persons with a history of angina or high blood pressure. The personal drug compartment 22 is electronically locked and can only be unlocked by a signal sent from the processor 24 or by a remotely located physician.

Figure 2:
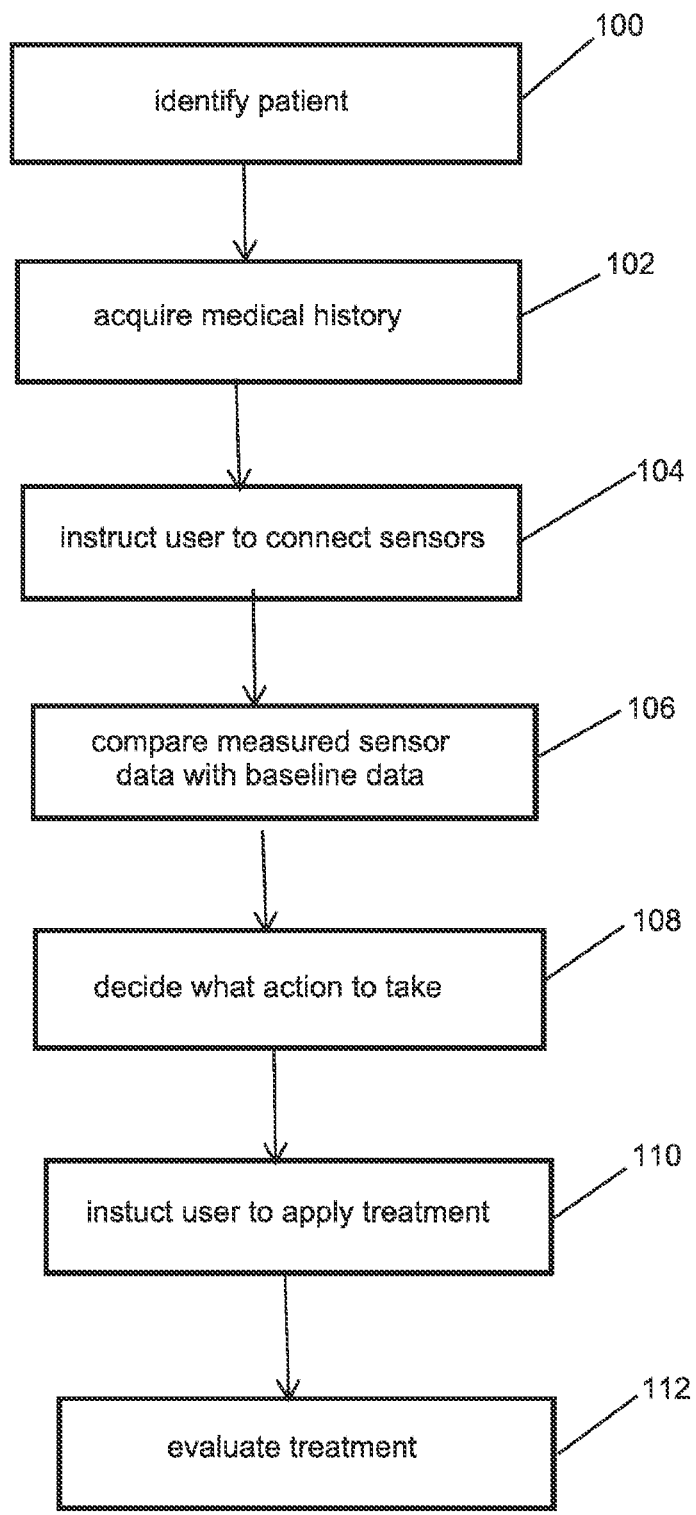
FIG. 2 is a flow chart that schematically shows the general scheme of the process carried out using the system of FIG. 1 for providing personalized medical treatment in an emergency situation.

FIG. 2 is a flow chart that schematically shows the general scheme of the process carried out using the system 10 for providing personalized medical treatment in an emergency situation.

Before beginning the process, an operator moves the patient and system close to each other and turns on the system. The operator may be the patient who recognizes known warning signs of the start of a medical emergency or another person who observes a patient undergoing a medical emergency. In other cases, initiation may be caused by measurements made by sensors in the monitoring module 12 that exceed a predefined limit. The control unit 16 of system 10 may be defined such that exceeding a predefined limit results in alerting the patient to log into the system or automatically turning the system on to begin treatment.

In some scenarios the treatment will be initiated without moving the patient and system close to each other. In one non-limiting example of such a scenario a continuous positive airway pressure (CPAP) is applied by a ventilator unit in equipment unit 20 to a patient being treated for sleep apnea while the patient sleeps. If a sensor indicates that the patient is having difficulty breathing then the ventilator unit is automatically converted into ventilation mode to actively treat, i.e. ventilate, the patient. In another non-limiting example, a patch routinely worn by a patient with an allergy to milk may be activated to deliver steroids upon anaphylaxis shock.

In the first step 100 the patient is identified to the system by at least one of the methods described herein above. If necessary, the processor will instruct the user either audibly or visually by means of display 32 to attach one or more of the sensors in sensor unit 18 used to identify a patient and to operate the appropriate components for identifying the patient from the equipment unit 20.

The second step 102 of the process is acquisition of the required medical history data by the control unit 12 of system 10. Data acquisition is done in one of the following ways:

Upon initial installation of the system in a specific location, a baseline test is done for people that regularly occupy that location. For each person a file is created and stored in memory 26 in the control unit 16 of the system. The file will contain physiological data such as sex, age, weight, height etc. as well as results of baseline vital signs measurements such as ECG, saturation, heart-rate, respiration rate etc. After identification of the patient by one of the methods described above, if the patient is known to the system, then his/her baseline data is accessed from their file.

If the patient's medical history is unknown, the system attempts to acquire the required medical data using one of the three options described herein above. Data acquired from a remote location such as a remote server or a private electronic medical record can be entered into the memory 26 in real-time. The transfer of the medical data from the remote location can be done by communication components 38 of control unit 16 that are capable of communicating with external locations via land-line or one or more wireless protocols 36 such as WiFi, cellular, or Bluetooth.

In the third step 104, based on the patient's medical history found in the second step and possibly information regarding the patient's general condition that is sensed and manually input to the system by the user, e.g. conscious or unconscious, high temperature, low temperature, and slow or fast pulse rate, the processor 12 will use display devices 32 to present the user with instructions how to attach specific sensors from sensor unit 18 to the patient's body to further monitor and provide more exact vital sign data.

In the fourth step 106 algorithms in software 28 will compare values of the sensor data with values for corresponding parameters from the baseline data in the patient's medical history. In addition or alternatively this comparison can also be made by a physician or emergency center 38 using data received remotely from the system.

In the fifth step 108 decision making algorithms in software 28 use inter alia the compared values from the fourth step 106 as well as information from the patient's medical history to determine what action should be taken. Specifically: if no further treatment is required, if the patient should be immediately evacuated to hospital, professional health care center, health care provider, or if treatment is to be applied at the location of the patient. Alternatively a physician or emergency center 38 may make the decision.

In the sixth step 110, if treatment is to be applied, the control unit 16 of system 10 will provide the user with specific instructions, e.g. the pressure and the amount of time to apply oxygen and/or to apply drugs from personalized drug unit 22. In certain situations the system can initiate treatment automatically, e.g. apply electric shock.

In the seventh step 112 the algorithms in software 28 may use information received from the sensors attached to the body of the patient to evaluate the effectiveness of the treatment i.e., whether the treatment should be changed, continued, or discontinued and whether, at this stage the patient should be transported to a hospital.

Steps 3-7 may be repeated until the patient's condition is ameliorated or an emergency professional arrives to the scene.

An optional feature of the system is the communication link 36 from communication components 34 that allow intervention, either automatic or manual, on from external sources 38, such as physicians (primarily the patient's personal physician if their contact details are entered into the patient's personal history in data storage 26), first responders, etc. Some of these remote personnel 38 may be authorized to enter suggestions or alter instructions provided by the system to the user. In addition, they may be authorized to remotely unlock the personal drug unit 22.

Commercially available defibrillators which are commonly found in public venues follow general outlines of defibrillations based only on the age (pediatric and adults) regardless of the specific medical status of the patient. Under professional care (e.g., Ambulance, ER) the patient suffering from shockable arrhythmias is treated using a more personalized protocol resulting in use of different placements of the pads, different intensity of the applied shock, different synchronization and timing of the shock together with drugs, oxygen, and monitoring synchronization between ventilation and defibrillation. In the professional surrounding this results in a significantly better outcome for the patient— even if the patient is new and his medical history is unknown or partially known to the professional care giver.

Advantageously, the present system enables personalized treatment and treatment protocol under non-professional care or non-medical surrounding. This system may also provide personalized treatment based on a complex history as can be seen from the following specific examples of the treatment the system will recommend for specific patients suffering from specific medical conditions. In these examples the advantage of the knowledge of a patient's medical history and/or online guidance from a remote medical care specialist in preventing misdiagnosis and improve efficiency of emergency treatment will be pointed out.

1. Primary Cardiac Case:

In this example, the system is applied to a patient with arrhythmia. According to the medical history the patient suffers from atrial fibrillation with hypotension and congestive heart failure and takes anticoagulants. The system is applied to the patient and, upon application, identification of the patient is performed and the patient's medical history revealed and taken into account. The initial system measurements after application: Blood pressure 80/40, Heart rate 140, and Saturation 86.

If there were no knowledge of the patient's medical history, he might have been initially misdiagnosed as suffering from undifferentiated shock, e.g. hemorrhagic, and time would be wasted looking for a bleeding site. Knowledge of the anticoagulant status will permit cardioversion.

2. Primary Respiratory Case:

In this example, the system is applied to a patient with chronic obstructive pulmonary disease (COPD), and asthma exacerbation.

The patient exhibits symptoms of dyspnea. According to the medical history in the system the patient is known to suffer from chronic bronchitis.

If there were no knowledge of the patient's medical history, the cause of the dyspnea wouldn't have been known and time might have been wasted with differential diagnosis such as congestive heart failure allergic reaction etc. Further there is a risk of a treatment error such as giving high flow oxygen to a COPD patient. Therefore, knowledge of the medical history in real time will allow suitable treatment such as low rate oxygen titration to blood oxygen saturation of 85-88%.

3. Primary Neurological Condition:

In this example, the system is applied to a patient with history of Transient Ischemic Attack (TIA) that takes aspirin. The system is applied to the patient due to the following complaints:

weakness of right side of body, difficulty speaking.

Diagnosis made by the system is suspected acute stroke.

If there were no knowledge of the patient's medical history, aspirin may have been applied again and risk of bleeding would have been increased.

4. Anaphylaxis:

In this example, the system is applied to a patient with known dairy milk allergies. Upon application of the system, identification of the patient is performed and the patient's medical history revealed and taken into account. The system is applied to the patient due to the following complaints: The patient feels dizziness, nauseated, looks irritated and flushed may have angioedema (swelling), and pruritus (itching). Because the system knows the patient's medical history, the patient is routinely monitored with a breathing sensor from sensor unit 18 that measures low shallow breath indicating a deterioration of saturation.

If there were no knowledge of the patient's medical history the clinical picture may deceive into diagnosis of asthma, undifferentiated shock or even a panic attack (Hyperventilation).

5. Anaphylactic Shock:

In this example the patient suffers from mild peanut allergy. The patient is in a restaurant and unknowingly eats a dish that includes peanuts. The observed symptom is difficulty in breathing. Due to the symptoms, he was connected to the system for identification and sensor measurement. The sensors for measuring breathing and saturation show low saturation and dyspnea. The patient was identified and his medical history was obtained.

Based on integrating the medical history and measurements of the sensors the diagnosis is anaphylactic shock and the suggested treatment is to apply epinephrine. A medical physician that has been contacted by the system approves the suggested treatment and sends a signal to unlock the drug unit 22. The user or the patient himself, if he is able, is instructed to withdraw a syringe containing epinephrine and how to administer the drug.

6. Transplant Patient Known to Have Undergone Liver Transplantation

In this example the patient is found in an unconscious state. After connecting the system to the patient the initial sensor measurements are the following: blood pressure 140/85; heart rate 110; saturation 95%; BPM 22; fever; and normal sinus rhythm in ECG.

If the patient's history was unknown, he might have been misdiagnosed as suffering from stroke (CVA—hemorrhage). However, since it was known to the system that he had undergone a liver transplant the system diagnosed his condition as unconsciousness due to liver failure, the following initial interventions were recommended by the system: apply pulse oximeter including Hemoglobinometer; apply ECG electrodes; apply etCO$_2$ sensor; check glucose level; and open a communication line with an emergency service.

7. Cancer—Patient is a Known Cancer Patient

The patient exhibits the following symptoms: fever and tachycardia, sepsis and leukocytopenia, which is measured using an optical sensor configured to observe white blood cells.

After connecting the system to the patient the initial sensor measurements are the following: blood pressure 140/85; heart rate 110; saturation 95%; BPM 22; fever; and normal sinus rhythm in ECG.

If the patient's history was unknown, he might have been misdiagnosed as having influenzas or any other trivial infection. However, since it was known to the system that this is a cancer patient undergoing chemotherapy suffering from sepsis the following the following initial interventions were recommended by the system: apply pulse oximeter including Hemoglobinometer; apply ECG electrodes; apply etCO$_2$ sensor; check glucose level; and open a communication line with an emergency service. Additionally, the patient should be quarantined and treated with broad-spectrum antibiotics as per advice from a qualified medical person at the emergency service.

8. Diabetic Patient—Hypoglycemia, Hyperglycemia

The patient has lost conciseness, on examination his pupils are dilated and unresponsive to light.

After connecting the system to the patient the initial sensor measurements are the following: blood pressure 150/90; heart rate 90; saturation 95%; BPM 20; fever; and normal sinus rhythm in ECG.

If the patient's history were unknown he could have been diagnosed as having suffered from severe brain damage and may have received incorrect treatment such as treatment for hypertension which in this case would have been harmful. However, since the patient's history known to the system divulged that patient is hypoglycemic with known diabetic associated ophthalmopathy the following initial interventions were recommended by the system: administer oxygen, apply pulse oximeter including Hemoglobinometer; apply ECG electrodes; apply etCO$_2$ sensor; check glucose level; apply glucose treatment; and open a communication line with an emergency service. The medical treatment, i.e. administration of oxygen, glucose treatment, and possibly giving aspirin are to be carried out assorcing to instructions received from the emergency service.

Although embodiments of the invention have been described by way of illustration, it will be understood that the invention may be carried out with many variations, modifications, and adaptations, without exceeding the scope of the claims.

The invention claimed is:

1. A system for determining information necessary for the immediate personalized treatment of a patient in a medical emergency in the absence of a trained medical professional, the system comprising:

A) a control unit comprising a processor, data storage elements, dedicated software, input devices, display devices, and communication components;

B) a sensor unit comprising sensors that are attachable to the patient's body to collect real-time data relating to the patient's vital signs, the sensors including an ECG sensor, a pulse oximeter, and one or more of: Electroencephalography (EEG) sensors, an ultrasound sensor, a capnograph to measure CO$_2$, a non-invasive blood pressure sensor, a sensor to measure respiration rate, one or more sensors to measure body temperature, a body weight assessing element, a glucometer, a Hemoglobinometer, an optical sensor configured to observe white blood cells, and a camera;

C) an equipment unit comprising an automated external defibrillator (AED) comprising an electric circuit connected to an internal battery or an external electricity source for generating current, ECG chest pads, and a ventilator unit comprising at least one of a turbine, a pressure generator, a closed mask, an open mask, a reservoir for a mask, an endotracheal tube, and a cylinder of pressurized oxygen or air;

wherein:

a) the system is located in a location where the identities of many of the persons who are present are known;

b) the data storage elements of the control unit contain files containing medical histories including known past non-conventional medical histories and base line vital signs data for each person whose identity is known;

c) the equipment unit comprises components that enable identification to the control unit of a person whose identity is known and for which baseline data exists in the data storage elements of the control unit, in at least one of the following ways: i) manual identification by allocating a specific key or by entering a unique number or a letter code for each person; ii) by an application on a portable device that is configured to communicate with the control unit; and iii) automatic identification by fingerprint or retinal scan, facial recognition, a signal broadcasted from a dedicated wearable device;

wherein after one of the persons for which a file exists in the data storage elements is identified as a patient, the processor and dedicated software are configured to perform the following:

i) determine if sensors in the sensor unit are required to monitor and collect vital sign data, wherein the determination of which sensors are required is based on the patient's medical history stored in the data storage elements and, if available, at least one of: ia) a monitoring module comprising sensors that are attached to the patient as he or she goes about their daily business wherein the monitoring module is equipped to transmit data about the patient's vital signs to the control unit; and ib) information regarding the patient's general condition that is sensed and manually input to the control unit by the user of the system;

ii) algorithms in the software compare values of the sensor data from the patient that are received at the control system with values for corresponding parameters from the baseline data in the patient's medical history;

iii) decision making algorithms in the software use the compared values of the sensor data with the baseline data and information from the patient's medical history to determine one of the following: iiia) if no further treatment is required; iiib) if the patient should be immediately evacuated to hospital, professional health care center, or a health care provider; and iiic) if treatment is to be applied at the location of the patient;

iv) if treatment is applied at the location of the patient, decision making algorithms in the software use the compared values of the sensor data with the baseline data and information from the patient's medical history and, if available, information regarding the patient's general condition that is sensed and manually input to the control unit by the user of the system to determine what treatment is required;

v) if treatment is applied at the location of the patient and it is necessary to activate the AED, the processor and software determine the placement of chest pads, intensity of applied shock, and timing of the applied shock; wherein:
  (a) the processor and software are configured to carry out methods for determining the placement of chest pads that include methods based on information recorded in the file containing medical history of the patient such as age, sex, weight, and presence of implanted devices; and
  (b) the processor and software are configured to carry out methods for determining the intensity and timing of the applied shock that include methods based on physiological clinical data as measured by sensors in the sensor unit and monitoring module in real time and the historical base line data in the file containing medical history of the patient;

vi) if treatment is applied at the location of the patient and it is necessary to activate the ventilator unit, the processor and software determine whether the ventilator unit should be activated to apply continuous positive airway pressure or to actively ventilate the patient and the pressure and amount of time to apply oxygen; wherein determination of when the ventilator should be activated is made according to the trend of changes in physiological parameters including at least one of: Saturation of peripheral oxygen (SpO2), End Tidal $CO_2$ (EtCO2), Peek Inspiratory Pressure (PIP), and minute volume (MV) that are measured by the pulse oximeter, capnography, and other sensors in the sensor unit;

vii) if treatment is applied at the location of the patient and it is necessary to activate both the AED and the ventilator unit, the processor and software determine synchronization and timing of shock administered by the AED together with oxygen administered by the ventilator unit; wherein synchronization and timing of the shock is determined by measurement of the ETCO2 by the capnograph in order to provide enough oxygenation to the coronary of the heart prior to the delivery of the shock;

viii) if treatment is applied at the location of the patient, the processor and software use information received from the sensors monitoring and collecting vital signs of the patient to evaluate the effectiveness of the treatment and whether the treatment should be changed, continued, or discontinued and whether, at this stage the patient should be transported to a hospital, professional health care center, or a health care provider; wherein if it is determined that the patient should be transported to a hospital, professional health care center, or a health care provider, the control unit is configured to allow activation of the communication components to transmit, to the destination to which the patient will be sent, information about the patient's health history and the treatment that has been administered.

2. The system of claim 1, wherein the input devices comprise at least one of a keyboard or graphical user interface, configured for imputing information into the processor and data storage elements.

3. The system of claim 1, wherein the display devices comprise at least one of a computer screen or a graphical user interface configured to display at least one of:
  a) personal information pertinent to the patient;
  b) the medical history of the patient;
  c) data from sensors attached to the patient;
  d) instructions generated by the software in the processor for applying sensors from the sensor unit to the patient; and
  e) instructions generated by the software in the processor for administrating treatment and using equipment from the treatment unit.

4. The system of claim 1, wherein the communication components are configured for WIFI, cellular, or Bluetooth two way communication between the control unit and the sensors in the sensor unit, the equipment in the treatment unit, and remotely located medical personnel, sensors, and databases and the communication components are configured for one way wired or wireless communication between the control unit and the personalized drug unit.

5. The system of claim 1, wherein the components in the equipment unit for identifying a patient comprise at least one of a fingerprint or retinal scanner, a bar code scanner, a camera for facial recognition, and a document scanner, each of which is connected to the communication components in the control unit.

6. The system of claim 1, wherein the medical histories for patient's whose identity is known to the system are obtained by at least one of the following methods:
  a) by contacting the database of the patient's health care provider;
  b) from a driver's license, identity card, or passport that is carried by the patient;
  c) from a medical alert bracelet worn by the patient;
  d) from testimony of persons accompanying the patient; and
  e) from a specialized pre-installed application containing the person's medical history on his/her personal smartphone.

7. The system of claim 1, wherein the monitoring module comprises components configured to issue alarm signals and to wirelessly transmit the alarm signals to the control unit if a medical emergency is detected.

8. The system of claim 1, wherein the system is located in a home or business and information relative to the treatment of their known past non-conventional medical histories can be entered directly into the system.

9. The system of claim 1, wherein the system is located at one of: a) an airplane or a cruise ship and passengers are required before boarding to provide their medical histories that will be stored in the data storage elements of the system, and b) in hotels at which visitors are required at check in to provide their medical histories that will be stored in the data storage elements of the system.

10. The system of claim 1, wherein all components of the sensor unit and the equipment unit are physically incorporated within a housing.

11. The system of claim 10, wherein at least one of the functions of the control unit is provided by components incorporated within the housing.

12. The system of claim 10, wherein at least one of the functions of the control unit is provided by at least one of: a personal computer, a laptop computer, a tablet computer, and a mobile communication device.

13. The system of claim 1, wherein all of the functions of the control unit are provided by at least one of: a personal computer, a laptop computer, a tablet computer, and a mobile communication device.

14. The system of claim 1, wherein the sensor unit contains specific types of sensors for use with patients suffering from specific known medical conditions.

15. The system of claim 1, wherein an operator of the system is one of: a) the patient who recognizes known warning signs of the start of a medical emergency; and b) another person who observes a patient undergoing a medical emergency.

\* \* \* \* \*